United States Patent
Okamoto

(10) Patent No.: US 10,969,362 B2
(45) Date of Patent: Apr. 6, 2021

(54) PARTICULAR-GAS CONCENTRATION-MEASURING APPARATUS AND PARTICULAR-GAS CONCENTRATION MEASURING SYSTEM

(71) Applicant: NGK INSULATORS, LTD., Aichi (JP)

(72) Inventor: Taku Okamoto, Nagoya (JP)

(73) Assignee: NGK INSULATORS, LTD., Nagoya (JP)

(*) Notice: Subject to any disclaimer, the term of this patent is extended or adjusted under 35 U.S.C. 154(b) by 120 days.

(21) Appl. No.: 16/263,043

(22) Filed: Jan. 31, 2019

(65) Prior Publication Data

US 2019/0250123 A1 Aug. 15, 2019

(30) Foreign Application Priority Data

Feb. 13, 2018 (JP) .............................. JP2018-023322

(51) Int. Cl.
*G01N 27/407* (2006.01)
*F01N 3/20* (2006.01)
(Continued)

(52) U.S. Cl.
CPC ......... *G01N 27/4074* (2013.01); *F01N 3/208* (2013.01); *F01N 3/2066* (2013.01);
(Continued)

(58) Field of Classification Search
CPC .......... G01N 27/4074; G01N 33/0054; G01N 27/301; G01N 27/4076; G01N 27/4077;
(Continued)

(56) References Cited

U.S. PATENT DOCUMENTS

2006/0151338 A1* 7/2006 Wang ................. G01N 27/4071
205/780.5
2009/0266142 A1* 10/2009 Wang ................. G01N 33/0054
73/23.32
(Continued)

FOREIGN PATENT DOCUMENTS

JP 2017-116371 A 6/2017

*Primary Examiner* — Maris R Kessel
*Assistant Examiner* — Joshua L Allen
(74) *Attorney, Agent, or Firm* — Mattingly & Malur, PC

(57) ABSTRACT

A particular-gas concentration-measuring apparatus measures a particular gas concentration being the concentration of a particular gas in a measurement-object gas. The particular-gas concentration-measuring apparatus comprises a particular-gas concentration derivation unit. The particular-gas concentration derivation unit causes an electromotive-force acquisition unit to acquire an electromotive force and derives a correction value compensating for the difference between a correction-value derivation electromotive force that is the electromotive force and the reference electromotive force at a correction-value derivation time. The correction-value derivation time is a time during which a sensing electrode is exposed to a correction-value derivation gas, the correction-value derivation gas being the measurement-object gas where neither ammonia nor a combustible gas is assumed to be included. The particular-gas concentration derivation unit derives the particular gas concentration using a corrected electromotive force determined by correcting the electromotive force with the correction value.

7 Claims, 6 Drawing Sheets

(51) Int. Cl.
*G01N 33/00* (2006.01)
*G01N 27/30* (2006.01)
*G01N 27/409* (2006.01)
*G01N 27/406* (2006.01)

(52) U.S. Cl.
CPC ......... *G01N 27/301* (2013.01); *G01N 27/409* (2013.01); *G01N 27/4067* (2013.01); *G01N 27/4076* (2013.01); *G01N 27/4077* (2013.01); *G01N 33/0054* (2013.01); *F01N 2560/021* (2013.01); *F01N 2610/02* (2013.01)

(58) Field of Classification Search
CPC ............. G01N 27/409; G01N 27/4067; G01N 27/4065; F01N 3/2066; F01N 3/208; F01N 2610/02; F01N 2560/021
See application file for complete search history.

(56) References Cited

U.S. PATENT DOCUMENTS

| | | | |
|---|---|---|---|
| 2011/0011152 A1* | 1/2011 | Ito | G01N 27/4077 73/23.31 |
| 2011/0048970 A1* | 3/2011 | Sugaya | G01N 27/419 205/781 |
| 2016/0356196 A1* | 12/2016 | Nakano | F01N 9/00 |
| 2017/0184538 A1 | 6/2017 | Okamoto et al. | |
| 2018/0283308 A1* | 10/2018 | Hayashita | F01N 9/005 |
| 2019/0112955 A1* | 4/2019 | Zhang | F02D 41/1463 |

* cited by examiner

PARTICULAR-GAS CONCENTRATION-MEASURING APPARATUS AND PARTICULAR-GAS CONCENTRATION MEASURING SYSTEM

The present application claims priority of Japanese Patent Application No. 2018-023322 filed on Feb. 13, 2018, the entire contents of which are incorporated herein by reference.

BACKGROUND OF THE INVENTION

1. Field of the Invention

The present invention relates to a particular-gas concentration-measuring apparatus and a particular-gas concentration-measuring system.

2. Description of the Related Art

Gas sensors that detect the concentration of a particular gas, such as ammonia concentration, in the measurement-object gas, such as automotive exhaust gas, have been known. For example, a mixed-potential gas sensor that includes a sensing electrode and a reference electrode disposed on an oxygen ion-conducting solid electrolyte is described in PTL 1.

CITATION LIST

Patent Literature

PTL 1: Japanese Unexamined Patent Application Publication No. 2017-116371

SUMMARY OF THE INVENTION

When the concentration of a particular gas is derived with a mixed-potential gas sensor, the correspondence between the concentration of the particular gas and electromotive force is predetermined before the derivation, and the concentration of the particular gas is determined on the basis of the correspondence and the output of the gas sensor (the electromotive force between the sensing and reference electrodes). The correspondence can be determined by, for example, testing a plurality of gases that include the particular gas at different known concentrations and measuring the output of the gas sensor for each of the gases.

However, the correspondence between the electromotive force and the concentration of the particular gas may deviate from the predetermined correspondence in the case where, for example, the gas sensor is used for a prolonged period of time. If the concentration of the particular gas is derived on the basis of the predetermined correspondence under the circumstances where the phenomenon has occurred, the accuracy of the measurement of the concentration of the particular gas may become degraded.

The present invention was made in order to address the above issues. A primary object of the present invention is to derive, with accuracy, the concentration of a particular gas in the measurement-object gas.

In order to achieve the primary object, the present invention employs the following items.

A particular-gas concentration-measuring apparatus according to the present invention is a particular-gas concentration-measuring apparatus that measures a particular gas concentration with a sensor element that includes a mixed potential cell, the mixed potential cell including a solid electrolyte body, a sensing electrode disposed on the solid electrolyte body, and a reference electrode disposed on the solid electrolyte body, the particular gas concentration being the concentration of a particular gas in a measurement-object gas, the particular gas being selected from ammonia and a combustible gas, the particular-gas concentration-measuring apparatus including:

an electromotive-force acquisition unit that acquires an electromotive force of the mixed potential cell which is generated under the condition where the sensing electrode is exposed to the measurement-object gas;

an oxygen-concentration acquisition unit that acquires an oxygen concentration in the measurement-object gas;

a memory unit that stores a measurement correspondence and reference electromotive force information, the measurement correspondence being the correspondence among the particular gas concentration, the oxygen concentration, and the electromotive force, the reference electromotive force information concerning a reference electromotive force that is the electromotive force generated under the condition where the sensing electrode is exposed to a gas that does not include ammonia or a combustible gas; and a particular-gas concentration derivation unit that executes a concentration derivation processing in which the particular gas concentration corresponding to the electromotive force and the oxygen concentration is derived on the basis of the measurement correspondence, the particular-gas concentration derivation unit causing, at a correction-value derivation time, the electromotive-force acquisition unit to acquire the electromotive force and deriving a correction value compensating for the difference between a correction-value derivation electromotive force that is the electromotive force and the reference electromotive force based on the reference electromotive force information, the correction-value derivation time being time during which the sensing electrode is exposed to a correction-value derivation gas, the correction-value derivation gas being the measurement-object gas that is under the condition where neither ammonia nor a combustible gas is assumed to be included, the particular-gas concentration derivation unit deriving, in the concentration derivation processing executed subsequent to the correction-value derivation time, the particular gas concentration using a corrected electromotive force determined by correcting the electromotive force with the correction value.

The particular-gas concentration-measuring apparatus is capable of deriving, with accuracy, the concentration of a particular gas in the measurement-object gas. The reasons are described below. The correspondence between the concentrations of a particular gas and oxygen in the measurement-object gas and the electromotive force of a mixed potential cell may change in the case where, for example, a sensor element is used for a prolonged period of time (hereinafter, this change is referred to as "change in output characteristics"). The inventors of the present invention found that the change in output characteristics is the change in which the electromotive force deviates (changes) by substantially the same amount independently of the concentrations of the particular gas and oxygen. Therefore, it is considered that using a correction value that compensates for the deviation of the electromotive force which has occurred due to the change in output characteristics enables the concentration of the particular gas to be derived with accuracy. The particular-gas concentration-measuring apparatus according to the present invention derives the correction value that compensates for the difference between a reference electromotive force and a correction-value derivation electromotive force. The reference electromotive force is the value derived from stored reference electromotive force information and is an electromotive force generated prior to the occurrence of the change in output characteristics. The correction-value derivation electromotive force is an electromotive force reflective of the deviation of the electromotive force when the change in output characteristics has occurred. Both correction-value derivation electromotive force and reference electromotive force are the electromotive forces generated under the condition where the influences of ammonia and a combustible gas are negligible (or considered negligible). Thus, the difference between the correction-value derivation electromotive force and the reference electromotive force corresponds to the deviation of the electromotive force which has occurred due to the change in output characteristics. Therefore, deriving the correction value that compensates for the above difference and using a corrected electromotive force calculated by correcting the electromotive force with the correction value subsequent to the correction-value derivation time enables the concentration of a particular gas in the measurement-object gas to be derived with accuracy even after the change in output characteristics has occurred.

The term "combustible gas" used herein refers to carbon monoxide (CO) and hydrocarbon (HC). That is, the particular gas is any of ammonia ($NH_3$), CO, and HC. The term "condition where neither ammonia nor a combustible gas is assumed to be included" used herein refers to the condition where the concentrations of these gases are low enough to neglect the influences of the gases on the electromotive force. An example of the "condition where neither ammonia nor a combustible gas is assumed to be included" is, for example, the condition where the concentrations of ammonia ($NH_3$), CO, and, HC in the measurement-object gas are less than 1 ppm or less than 0.1 ppm. The expression "acquire an electromotive force" used herein also refers to the act of acquiring information convertible into the electromotive force or information considered equivalent to the electromotive force. The expression "acquire the concentration of oxygen" used herein also refers to the act of acquiring information convertible into the concentration of oxygen or information considered equivalent to the concentration of oxygen.

In the particular-gas concentration-measuring apparatus according to the present invention, the measurement-object gas may be an exhaust gas emitted from an internal-combustion engine, and the correction-value derivation gas may be an exhaust gas emitted from the internal-combustion engine during fuel cut-off. Since the amount of ammonia and a combustible gas included in the exhaust gas emitted during fuel cut-off is negligibly small, using the exhaust gas emitted during the above period as a correction-value derivation gas for deriving the correction value enables the correction value to be derived appropriately.

In such a case, the particular-gas concentration-measuring apparatus according to the present invention may include an information acquisition unit that acquires fuel cut-off execution information concerning execution of the fuel cut-off, and the particular-gas concentration derivation unit may detect the correction-value derivation time on the basis of the fuel cut-off execution information. This enables the particular-gas concentration derivation unit to detect the correction-value derivation time appropriately.

In the particular-gas concentration-measuring apparatus according to the present invention, the correction-value derivation gas may be the measurement-object gas which is under the condition where the measurement-object gas can be assumed to be the atmosphere. Since the amount of ammonia and a combustible gas included in the atmosphere is negligibly small, using the exhaust gas emitted during the above period as a correction-value derivation gas for deriving the correction value enables the correction value to be derived appropriately. Note that, the exhaust gas emitted during fuel cut-off is a type of the measurement-object gas which is under the condition where the measurement-object gas can be assumed to be the atmosphere.

In such a case, the particular-gas concentration derivation unit may determine whether or not the oxygen concentration acquired by the oxygen-concentration acquisition unit falls within a predetermined range in which the oxygen concentration is assumed to be equal to the oxygen concentration in the atmosphere and detect the correction-value derivation time on the basis of the results. This enables the particular-gas concentration derivation unit to detect the correction-value derivation time by a relatively easy and simple method.

In the particular-gas concentration-measuring apparatus according to the present invention, the reference electromotive force information may be information that includes the correspondence between the oxygen concentration in a gas which does not include ammonia or a combustible gas and the reference electromotive force generated when the sensing electrode is exposed to the gas, and the particular-gas concentration derivation unit may derive the reference electromotive force that corresponds to the oxygen concentration in the correction-value derivation gas, which is acquired by the oxygen-concentration acquisition unit, on the basis of the reference electromotive force information and derive the correction value on the basis of the reference electromotive force and the correction-value derivation electromotive force. Even when the sensing electrode is exposed to a gas that does not include ammonia or a combustible gas, the reference electromotive force may vary with the oxygen concentration in the gas. The same applies to correction-value derivation electromotive force. Thus, storing the correspondence between the oxygen concentration and the reference electromotive force and using the reference electromotive force that corresponds to the oxygen concentration in the correction-value derivation gas for deriving the correction value enables a further appropriate correction value to be derived. Consequently, the concentration of the particular gas can be measured with further accuracy.

A particular-gas concentration-measuring system according to the present invention includes the particular-gas concentration-measuring apparatus according to any one of the above aspects and the above-described sensor element. Accordingly, the particular-gas concentration-measuring system has the same advantageous effects as the particular-gas concentration-measuring apparatus according to the present invention. That is, for example, the particular-gas concentration-measuring system is capable of deriving, with accuracy, the concentration of a particular gas in the measurement-object gas.

DETAILED DESCRIPTION OF THE INVENTION

Figure 1:
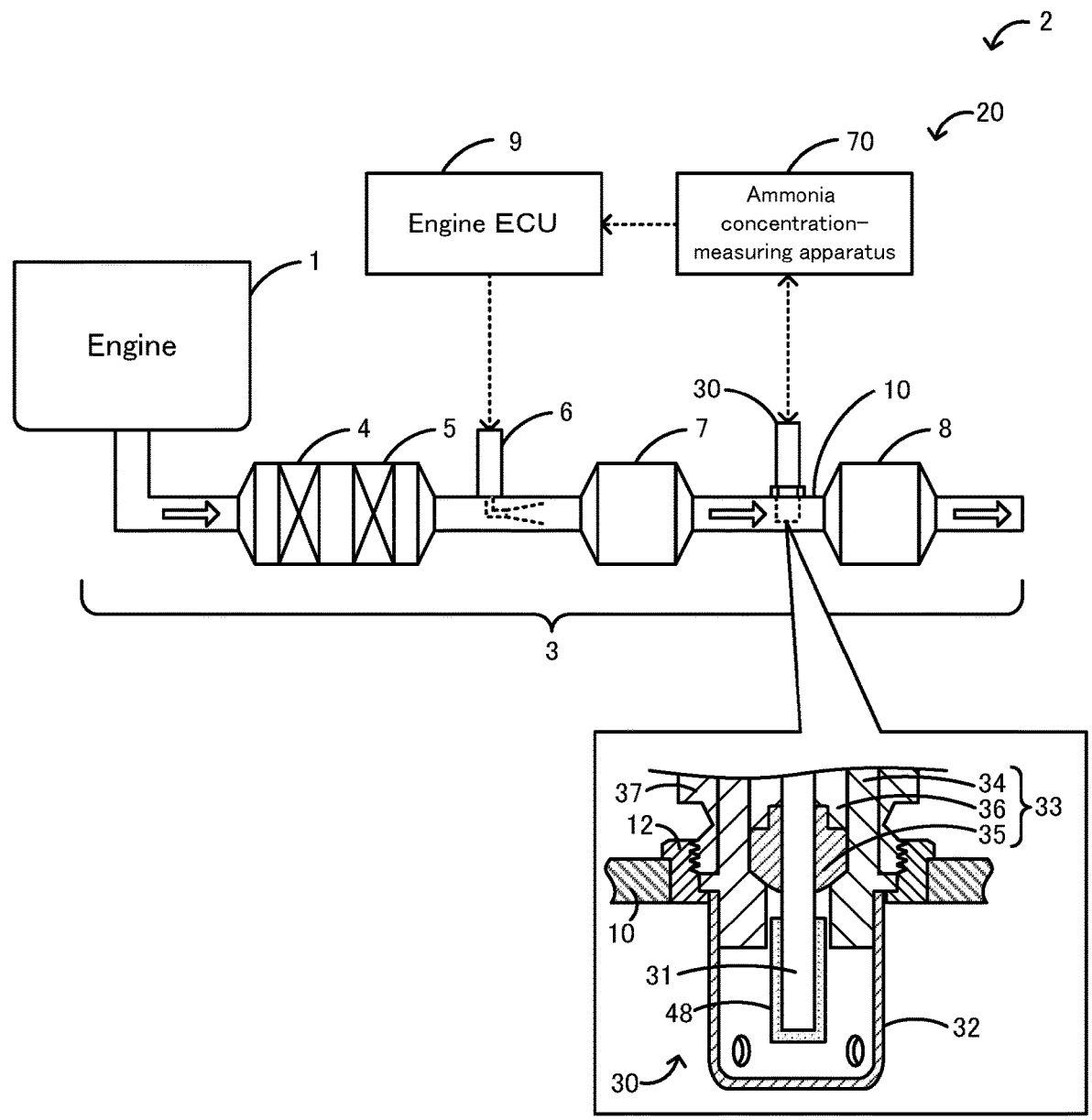
FIG. 1 is a diagram illustrating a system 2 for treating an exhaust gas emitted from an engine 1.
Figure 2:
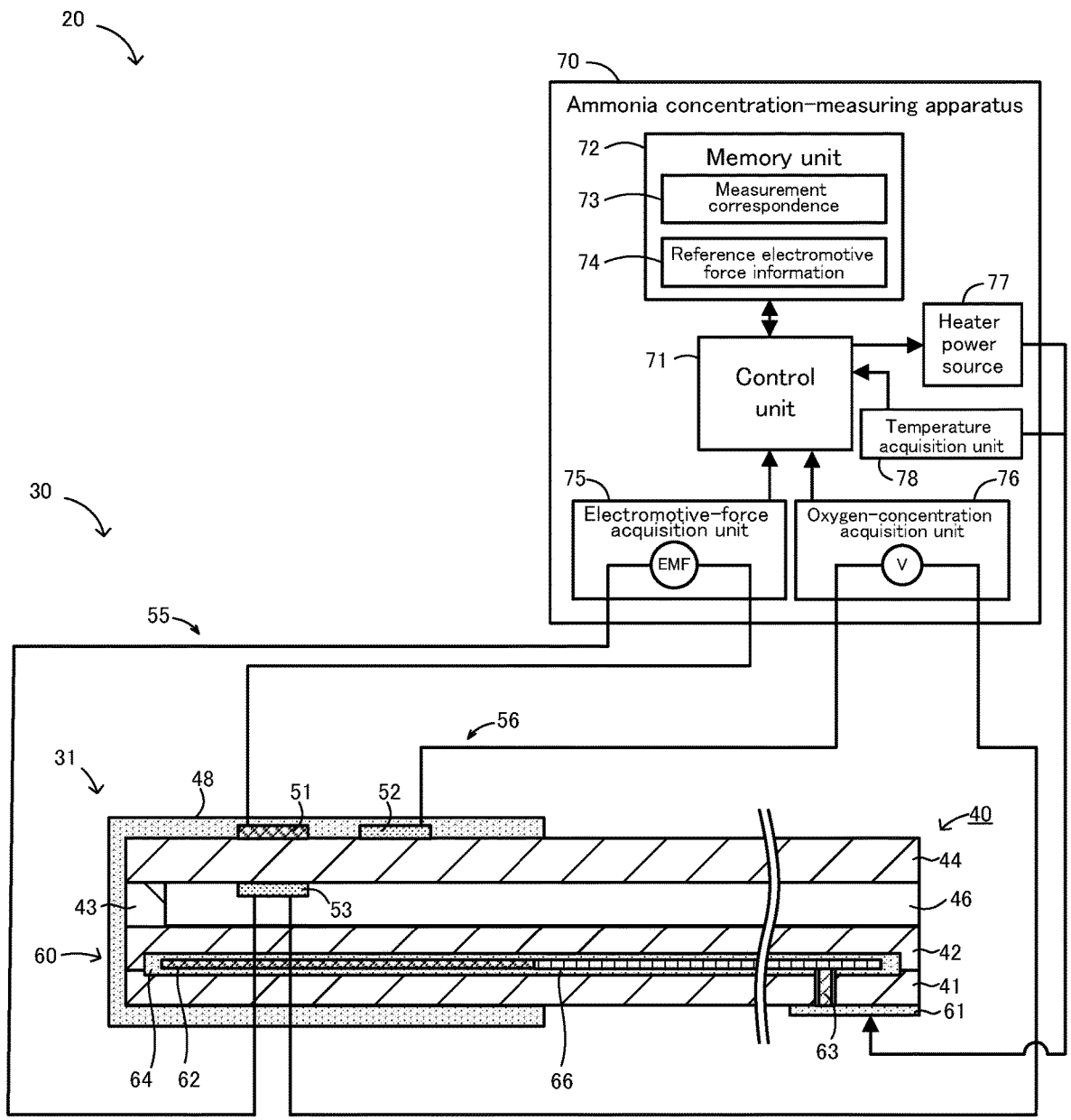
FIG. 2 is a diagram illustrating an ammonia concentration-measuring system 20.

Embodiments of the present invention are described below with reference to the attached drawings. FIG. 1 is a diagram illustrating a system 2 for treating an exhaust gas emitted from an engine 1, the system 2 including an ammonia concentration-measuring system 20 according to an embodiment of the present invention. FIG. 2 is a diagram illustrating the ammonia concentration-measuring system 20, which measures the concentration of a particular gas (in this embodiment, ammonia) in the exhaust gas.

The exhaust gas-treating system 2 is a system for treating an exhaust gas emitted from the engine 1, which is the measurement-object gas. The engine 1 is a diesel engine in this embodiment. The exhaust gas-treating system 2 includes, as illustrated in FIG. 1, an exhaust gas passage 3 connected to the engine 1 and an ammonia concentration-measuring system 20 that includes a gas sensor 30 disposed in the exhaust gas passage 3. The exhaust gas-treating system 2 includes a DOC (diesel oxidation catalyst) 4, a DPF (diesel particulate filter) 5, an injector 6, an SCR (selective catalytic reduction) 7, the gas sensor 30, and an ASC (ammonia slip catalyst) 8, which are arranged in this order in the direction of the flow of the exhaust gas. The DOC 4 is one of the oxidation catalysts included in the exhaust gas-treating system 2. The DOC 4 detoxifies the exhaust gas by converting HC and CO included in the exhaust gas into water and carbon dioxide. The DPF 5 captures PM included in the exhaust gas. The injector 6 is a device that injects at least one selected from ammonia and a substance capable of producing ammonia (e.g., urea) into the exhaust pipe so as to feed the substance to the SCR 7. In this embodiment, the injector 6 injects urea into the exhaust pipe, and the urea is decomposed by hydrolysis to produce ammonia. The SCR 7 reduces nitrogen oxides (NOx) included in the exhaust gas into harmless $N_2$ and $H_2O$ by using the ammonia fed from the injector 6 into the exhaust pipe. The exhaust gas passed through the SCR 7 flows through a pipe 10. The gas sensor 30 is attached to the pipe 10. The ASC 8 is disposed in the pipe 10 on the downstream side. The ASC 8 is one of the oxidation catalysts included in the exhaust gas-treating system 2 and referred to also as "downstream DOC", in contrast to the DOC 4 (upstream DOC). The ASC 8 oxidizes excess ammonia included in the exhaust gas passed through the SCR 7 into harmless $N_2$ and $H_2O$. The exhaust gas passed through the ASC 8 is released into, for example, the atmosphere.

The ammonia concentration-measuring system 20 includes the gas sensor 30 and an ammonia concentration-measuring apparatus 70 electrically connected to the gas sensor 30. The gas sensor 30 is an ammonia sensor that generates an electrical signal responsive to the concentration of excess ammonia in the measurement-object gas which has been passed through the SCR 7 and is present inside the pipe 10. The gas sensor 30 serves also as an oxygen sensor that generates an electrical signal responsive to the oxygen concentration in the measurement-object gas. That is, the gas sensor 30 is a multisensor. The ammonia concentration-measuring apparatus 70 derives the ammonia concentration in the measurement-object gas on the basis of the electrical signal generated by the gas sensor 30 and sends the ammonia concentration to an engine ECU 9. The engine ECU 9 controls the amount of urea injected from the injector 6 into the exhaust pipe such that the concentration of the excess ammonia approaches zero. Details of the ammonia concentration-measuring system 20 are described below.

The gas sensor 30 includes, as illustrated in the enlarged cross-sectional view of FIG. 1, a sensor element 31; a protective cover 32 that covers and protects one end of the sensor element 31 in the longitudinal direction, that is, the front end (in FIG. 1, the lower end) of the sensor element 31; an element-fixing portion 33 that fixes the sensor element 31 in an enclosed manner; and a nut 37 attached to the element-fixing portion 33. The one end of the sensor element 31 is covered with a porous protective layer 48.

The protective cover 32 is a closed-end cylindrical cover that covers the one end of the sensor element 31. Although the protective cover 32 illustrated in FIG. 1 is a single-layer cover, the protective cover 32 may be a cover constituted by two or more layers which includes, for example, an inner protective cover and an outer protective cover. The protective cover 32 has a plurality of holes formed therein through which the measurement-object gas is passed through the inside of the protective cover 32. The one end of the sensor element 31 and the porous protective layer 48 are disposed inside the space surrounded by the protective cover 32.

The element-fixing portion 33 includes a cylindrical main metal fitting 34; a ceramic support 35 enclosed in an open-hole formed inside the main metal fitting 34; and a compact 36 enclosed in the open-hole formed inside the main metal fitting 34, the compact 36 being produced by molding a power of a ceramic, such as talc, into shape. The sensor element 31 penetrates the element-fixing portion 33 in the longitudinal direction. The compact 36 is compressed between the main metal fitting 34 and the sensor element 31. This enables the compact 36 to seal the open-hole formed inside the main metal fitting 34 and fix the sensor element 31.

The nut 37 is fixed coaxially with the main metal fitting 34 and has an external thread formed on the outer periphery thereof. The external thread of the nut 37 is inserted into the inside of a mounting member 12 joined to the pipe 10 by welding, the mounting member 12 having an internal thread formed in the inner periphery thereof. This enables the gas sensor 30 to be fixed to the pipe 10 while the one end of the sensor element 31 and the protective cover 32 are protruded inside the pipe 10.

The sensor element 31 is described with reference to FIG. 2. The cross-sectional view of the sensor element 31 illustrated in FIG. 2 shows a cross section of the sensor element 31 taken along the central axis in the longitudinal direction (a cross section taken in the vertical direction in FIG. 1). The sensor element 31 includes a base 40 composed of an oxygen ion-conducting solid electrolyte; a sensing electrode 51 and an auxiliary electrode 52 that are disposed on the top surface of the base 40 at the one end of the sensor element 31 (in FIG. 1, the lower end; in FIG. 2, the left-side end); a reference electrode 53 disposed inside the base 40; and a heater unit 60 with which the temperature of the base 40 is adjusted.

The base 40 includes four layers, that is, a first substrate layer 41, a second substrate layer 42, a spacer layer 43, and a solid electrolyte layer 44 that are layers composed of an oxygen ion-conducting solid electrolyte, such as zirconia (ZrO$_2$), the four layers being stacked on top of one another in this order in an upward direction in FIG. 2. The base 40 has a plate-like structure. The solid electrolytes constituting the four layers are dense and hermetic. The periphery of a portion of the base 40 which is present inside the protective cover 32 is exposed to the measurement-object gas that has been introduced inside the protective cover 32. The base 40 has a reference-gas introduction space 46 formed in a portion of the base 40 which is interposed between the top surface of the second substrate layer 42 and the bottom surface of the solid electrolyte layer 44, the sides of the portion being defined by the side surfaces of the spacer layer 43. The reference-gas introduction space 46 has an opening formed at the other end (in FIG. 2, the right-side end) of the sensor element 31, which is far from the one end of the sensor element 31. The reference-gas introduction space 46 is fed with a reference gas used for the measurement of ammonia and oxygen concentrations, such as the atmosphere. The layers constituting the base 40 may be substrates composed of a zirconia solid electrolyte to which 3 to 15 mol % yttria (Y$_2$O$_3$) has been added as a stabilizer (yttria stabilized zirconia (YSZ) substrates).

The sensing electrode 51 is a porous electrode disposed on the top surface of the solid electrolyte layer 44 in the base 40 illustrated in FIG. 2. The sensing electrode 51, the solid electrolyte layer 44, and the reference electrode 53 constitute a mixed potential cell 55. In the mixed potential cell 55, a mixed potential (electromotive force EMF) responsive to the ammonia concentration in the measurement-object gas is generated at the sensing electrode 51. The electromotive force EMF between the sensing electrode 51 and the reference electrode 53 is used for deriving the ammonia concentration in the measurement-object gas. The sensing electrode 51 is composed primarily of a material that is capable of generating a mixed potential responsive to the ammonia concentration and has a sensitivity for detecting ammonia concentration. The sensing electrode 51 may include a precious metal, such as gold (Au), as a principal constituent. The principal constituent of the sensing electrode 51 is preferably an Au—Pt alloy. The term "principal constituent" used herein refers to a constituent having the highest proportion (atm %, atomic weight ratio) among all the constituents. The degree of concentration (=Proportion of Au [atom %]/Proportion of Pt [atom %]) of the sensing electrode 51 which is determined by at least one method selected from X-ray photoelectron spectroscopy (XPS) and Auger electron spectroscopy (AES) is preferably 0.1 or more and is more preferably 0.3 or more. The degree of concentration of the sensing electrode 51 is the degree of surface concentration in the surfaces of the precious metal particles included in the sensing electrode 51. The proportion [atom %] of Au is the proportion of Au present in the surfaces of the precious metal particles included in the sensing electrode 51. Similarly, the proportion [atom %] of Pt is the proportion of Pt present in the surfaces of the precious metal particles included in the sensing electrode 51. The surfaces of the precious metal particles may be the surface of the sensing electrode 51 (e.g., in FIG. 2, the top surface) or a fracture surface of the sensing electrode 51. For example, in the case where the surface of the sensing electrode 51 (in FIG. 2, the top surface) is exposed, the degree of concentration can be measured on the surface of the sensing electrode 51 and XPS may be used for the measurement. In such a case, alternatively, the degree of concentration may be measured by AES. In the case where the sensing electrode 51 is covered with the porous protective layer 48 as in this embodiment, the degree of concentration is determined by analyzing a fracture surface of the sensing electrode 51 (in FIG. 2, the fracture surface that extends in the vertical direction) by XPS or AES. The larger the degree of concentration, the lower the proportion of Pt present in the surface of the sensing electrode 51 and the smaller the likelihood of ammonia included in the measurement-object gas being decomposed by Pt in the vicinity of the sensing electrode 51. Consequently, the larger the degree of concentration, the higher the accuracy with which the ammonia concentration-measuring system 20 derives the ammonia concentration. The upper limit for the degree of concentration is not specified. For example, the sensing electrode 51 does not necessarily include Pt. The entirety of the sensing electrode 51 may be composed of Au. The sensing electrode 51 may be a porous cermet electrode composed of an Au—Pt alloy and zirconia.

The auxiliary electrode 52 is a porous electrode disposed on the top surface of the solid electrolyte layer 44, similarly to the sensing electrode 51. The auxiliary electrode 52, the solid electrolyte layer 44, and the reference electrode 53 constitute an electrochemical concentration cell 56. In the concentration cell 56, an electromotive force difference V that is a potential difference responsive to the difference in the oxygen concentration between the auxiliary electrode 52 and the reference electrode 53 is generated. The electromotive force difference V is used for deriving the oxygen concentration (oxygen partial pressure) in the measurement-object gas. The auxiliary electrode 52 may be composed of any precious metal having catalytic activity. For example, the auxiliary electrode 52 may be composed of Pt, Ir, Rh, Pd, or an alloy that includes at least one metal selected from the above elements. In this embodiment, the auxiliary electrode 52 is composed of Pt. The auxiliary electrode 52 may be a porous cermet electrode composed of Pt and zirconia.

The reference electrode 53 is a porous electrode disposed on the bottom surface of the solid electrolyte layer 44, that is, on a surface of the solid electrolyte layer 44 which is opposite to the surface on which the sensing electrode 51 and the auxiliary electrode 52 are disposed. The reference electrode 53 is exposed to the inside of the reference-gas introduction space 46 and fed with the reference gas (in this embodiment, the atmosphere) present in the reference-gas introduction space 46. The potential of the reference electrode 53 is a reference with which the electromotive force EMF and the electromotive force difference V are measured. The reference electrode 53 may be composed of any precious metal having catalytic activity. For example, the reference electrode 53 may be composed of Pt, Ir, Rh, Pd, or an alloy that includes at least one metal selected from the above elements. In this embodiment, the reference electrode 53 is composed of Pt. The reference electrode 53 may be a porous cermet electrode composed of Pt and zirconia.

The porous protective layer 48 covers the surface of the sensor element 31, which includes the sensing electrode 51 and the auxiliary electrode 52. For example, the porous protective layer 48 reduces the likelihood of cracks being formed in the sensor element 31 by moisture and the like included in the measurement-object gas being deposited on the sensor element 31. The porous protective layer 48 includes, for example, any of alumina, zirconia, spinel, cordierite, titania, and magnesia as a principal constituent. In this embodiment, the porous protective layer 48 is composed of alumina. The thickness of the porous protective layer 48 is, for example, 20 to 1000 μm. The porosity of the porous protective layer 48 is, for example, 5% to 60%. The sensor element 31 does not necessarily include the porous protective layer 48.

The heater unit 60 heats the base 40 (in particular, the solid electrolyte layer 44) and keeps the temperature of the base 40 in order to activate the solid electrolyte constituting the base 40 and thereby enhance the oxygen ion-conductivity. That is, the heater unit 60 is responsible for temperature control. The heater unit 60 includes a heater electrode 61, a heater 62, a through-hole 63, a heater insulating layer 64, and a lead wire 66. The heater electrode 61 is an electrode arranged to come into contact with the bottom surface of the first substrate layer 41. The heater electrode 61 is connected to a heater power source 77 included in the ammonia concentration-measuring apparatus 70.

The heater 62 is an electrical resistance element interposed between the first substrate layer 41 and the second substrate layer 42 disposed above and below the heater 62. The heater 62 is connected to the heater electrode 61 with the lead wire 66 and the through-hole 63. The heater 62 generates heat upon being fed with electric power from the heater power source 77 through the heater electrode 61 to heat the base 40 constituting the sensor element 31 and keep the temperature of the base 40. The output of the heater 62 can be controlled using a temperature sensor (in this embodiment, a temperature acquisition unit 78) such that the mixed potential cell 55 and the concentration cell 56 (in particular, the solid electrolyte layer 44) are operated at a predetermined operating temperature. The operating temperature is preferably set to 450° C. or more in order to appropriately activate the solid electrolyte layer 44 of the mixed potential cell 55. The operating temperature may be set to 600° C. or more and 700° C. or less. The operating temperature may be set to 650° C. or more and 660° C. or less. The heater insulating layer 64 is a porous alumina insulating layer that is disposed on the top and bottom surfaces of the heater 62 and composed of an insulator, such as alumina.

The ammonia concentration-measuring apparatus 70 is an apparatus that measures the ammonia concentration in the measurement-object gas with the sensor element 31. The ammonia concentration-measuring apparatus 70 serves also as an apparatus for controlling the sensor element 31. The ammonia concentration-measuring apparatus 70 includes a control unit 71 (an example of the particular-gas concentration derivation unit and the information acquisition unit), a memory unit 72, an electromotive-force acquisition unit 75, an oxygen-concentration acquisition unit 76, a heater power source 77, and a temperature acquisition unit 78.

The control unit 71 is responsible for the control of the entire apparatus. The control unit 71 is, for example, a microprocessor that includes a CPU, a RAM, and the like. The memory unit 72 stores processing programs and data used by the control unit 71. The memory unit 72 stores a measurement correspondence 73 and reference electromotive force information 74 (details are described below). The electromotive-force acquisition unit 75 is a voltage detection circuit that is connected to the sensing electrode 51 and the reference electrode 53 of the mixed potential cell 55 to acquire an electromotive force EMF. The oxygen-concentration acquisition unit 76 is a voltage detection circuit that is connected to the auxiliary electrode 52 and the reference electrode 53 of the concentration cell 56 to acquire an electromotive force difference V as oxygen concentration. The electromotive-force acquisition unit 75 and the oxygen-concentration acquisition unit 76 output the electromotive force EMF and the electromotive force difference V, respectively, to the control unit 71. The control unit 71 derives an ammonia concentration that corresponds to the electromotive force EMF and the oxygen concentration in the measurement-object gas on the basis of the electromotive force EMF, the oxygen concentration that corresponds to the electromotive force difference V, and the measurement correspondence 73. The heater power source 77 is a power source with which the heater 62 is fed with electric power. The control unit 71 controls the output of the heater 62. The temperature acquisition unit 78 is a module that acquires a value (in this embodiment, resistance) responsive to the temperature of the heater 62. The temperature acquisition unit 78 is connected to, for example, the heater electrode 61 and acquires the resistance of the heater 62 by passing a minute electric current through the heater 62 and measuring the voltage.

Although not illustrated in FIG. 2, the sensing electrode 51, the auxiliary electrode 52, and the reference electrode 53 are electrically connected to a plurality of lead wires that extend toward the other end of the sensor element 31 (in FIG. 2, the right-side end) in a one-to-one relationship. The electromotive-force acquisition unit 75 and the oxygen-concentration acquisition unit 76 measure the electromotive force EMF and the electromotive force difference V, respectively, via the lead wires.

Figure 3:
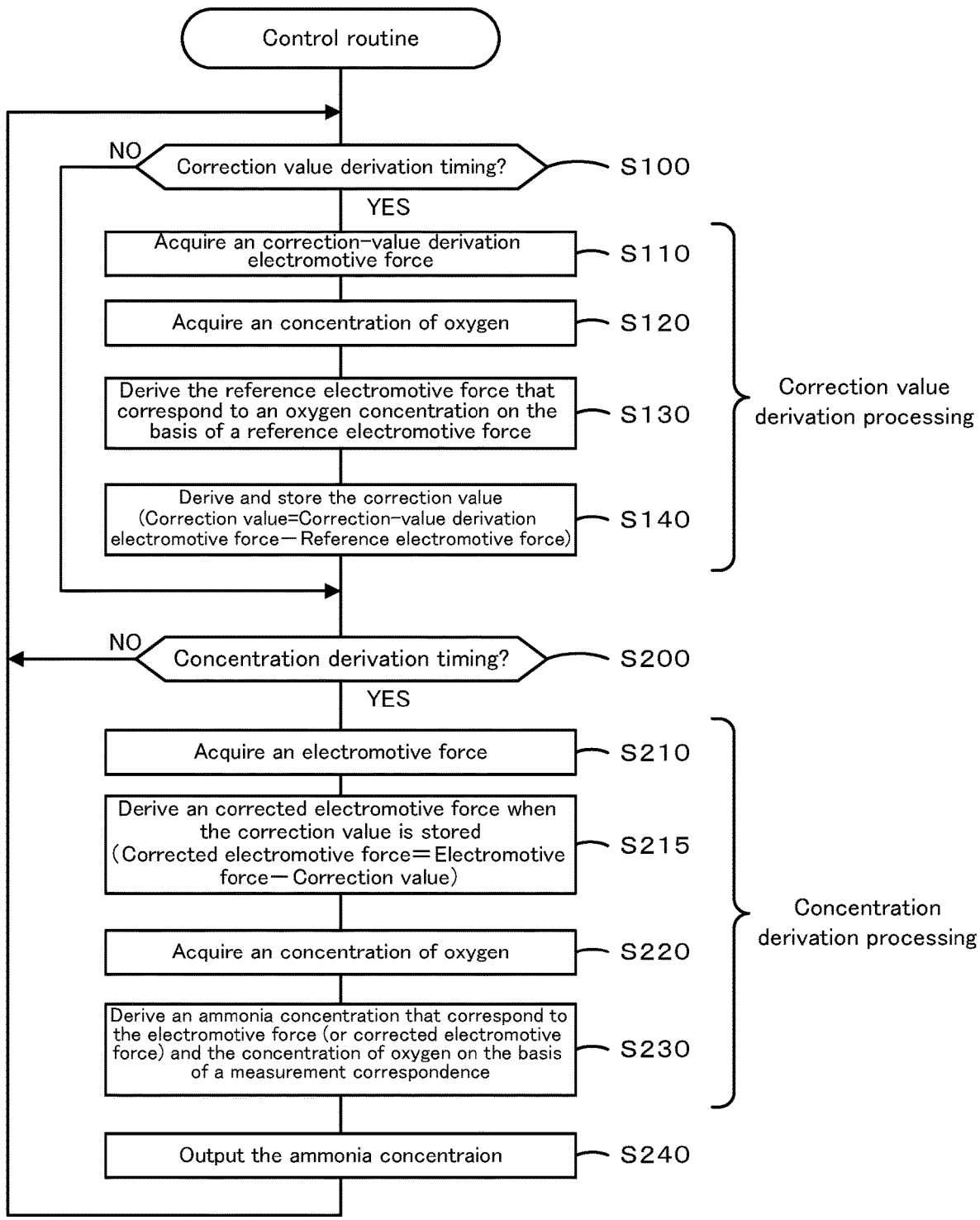
FIG. 3 is a flowchart illustrating an example control routine.

The operation of the above-described ammonia concentration-measuring system 20 is described below. FIG. 3 is a flowchart illustrating an example of the control routine executed by the control unit 71. The control unit 71 stores the routine in, for example, the memory unit 72 and starts the routine upon receiving a command to start the derivation of ammonia concentration from the engine ECU 9. Prior to the measurement, the control unit 71 causes the heater 62 to generate heat while controlling the output of the heater power source 77 in order to control the temperatures of the mixed potential cell 55 and the concentration cell 56 to be a predetermined operating temperature (e.g., a temperature of 600° C. or more and 700° C. or less). The control unit 71 controls the operating temperature by controlling the output of the heater power source 77 such that, for example, the temperature (in this embodiment, resistance) of the heater 62 which is acquired by the temperature acquisition unit 78 is a predetermined value. The exhaust gas emitted from the engine 1 has been passed into the protective cover 32. That is, the sensing electrode 51 and the auxiliary electrode 52 have been exposed to the exhaust gas.

At the start of the control routine, the control unit 71 determines whether or not it is correction-value derivation time to derive the correction value used for deriving ammonia concentration (Step S100). The correction-value derivation time is the time during which the sensing electrode 51 is exposed to a correction-value derivation gas, which is the measurement-object gas that is under the condition where neither ammonia nor a combustible gas is assumed to be included. In this embodiment, the correction-value derivation gas is an exhaust gas emitted from the engine 1 during fuel cut-off. The control unit 71 determines whether or not fuel cut-off execution information concerning the execution of fuel cut-off of the engine 1 has been acquired from the engine ECU 9, for example, at predetermined time intervals. Upon receiving the fuel cut-off execution information, the control unit 71 determines that the fuel cut-off of the engine 1 has been executed. After the lapse of a predetermined amount of delay time since the acquisition of the fuel cut-off execution information, the control unit 71 determines that the sensing electrode 51 is exposed to the exhaust gas emitted during fuel cut-off, that is, it is the correction-value derivation time. The amount of delay time is predetermined on the basis of the amount of time it takes for the measurement-object gas to flow from the engine 1 to the gas sensor 30.

When the control unit 71 determines that it is not the correction-value derivation time in Step S100, the control unit 71 determines whether or not it is the time to derive ammonia concentration (Step S200). The control unit 71 determines that it is the concentration derivation time, for example, after the lapse of a predetermined amount of time or upon receiving a command to derive concentration from the engine ECU 9. When the control unit 71 determines that it is the concentration derivation time in Step S200, the control unit 71 executes a concentration derivation processing in Steps S210 to S230.

In the concentration derivation processing, first, the control unit 71 acquires the electromotive force EMF of the mixed potential cell 55 with the electromotive-force acquisition unit 75 (Step S210). Consequently, the control unit 71 acquires the electromotive force EMF of the mixed potential cell 55 which is generated under the condition where the sensing electrode 51 is exposed to the measurement-object gas. In the mixed potential cell 55, electrochemical reactions, such as oxidation of ammonia included in the measurement-object gas and ionization of oxygen included in the gas, occur at the three-phase interface between the sensing electrode 51, the solid electrolyte layer 44, and the measurement-object gas, and a mixed potential is consequently generated at the sensing electrode 51. Accordingly, the electromotive force EMF is responsive to the concentrations of ammonia and oxygen in the measurement-object gas. Subsequently, in the case where the correction value has been derived, the control unit 71 derives a corrected electromotive force by using the correction value (Step S215). However, since the case where the correction value has not been derived is described above, the control unit 71 skips the derivation of the corrected electromotive force.

The control unit 71 acquires the electromotive force difference V of the concentration cell 56 as the oxygen concentration in the measurement-object gas with the oxygen-concentration acquisition unit 76 (Step S220). In the concentration cell 56, an electromotive force difference V occurs between the auxiliary electrode 52 and the reference electrode 53 in response to the difference between the oxygen concentration in the measurement-object gas and the oxygen concentration in the atmosphere present in the reference-gas introduction space 46. Although hydrocarbons, $NH_3$, CO, NO, and $NO_2$ included in the measurement-object gas may be reduced or oxidized by the catalytic action of Pt included in the auxiliary electrode 52, the reduction-oxidation reaction hardly affects the oxygen concentration in the measurement-object gas because the concentrations of these gas components in the measurement-object gas are commonly much lower than the oxygen concentration in the measurement-object gas. Therefore, the electromotive force difference V is responsive to the oxygen concentration in the measurement-object gas. The memory unit 72 stores the correspondence between the electromotive force difference V and oxygen concentration which has been derived by experiment or the like. The control unit 71 acquires the oxygen concentration in the measurement-object gas which is converted from the electromotive force difference V on the basis of the correspondence. The control unit 71 may conduct either of Steps S210 and S220 first. Alternatively, Steps S210 and S220 may be conducted in parallel.

Figure 4:
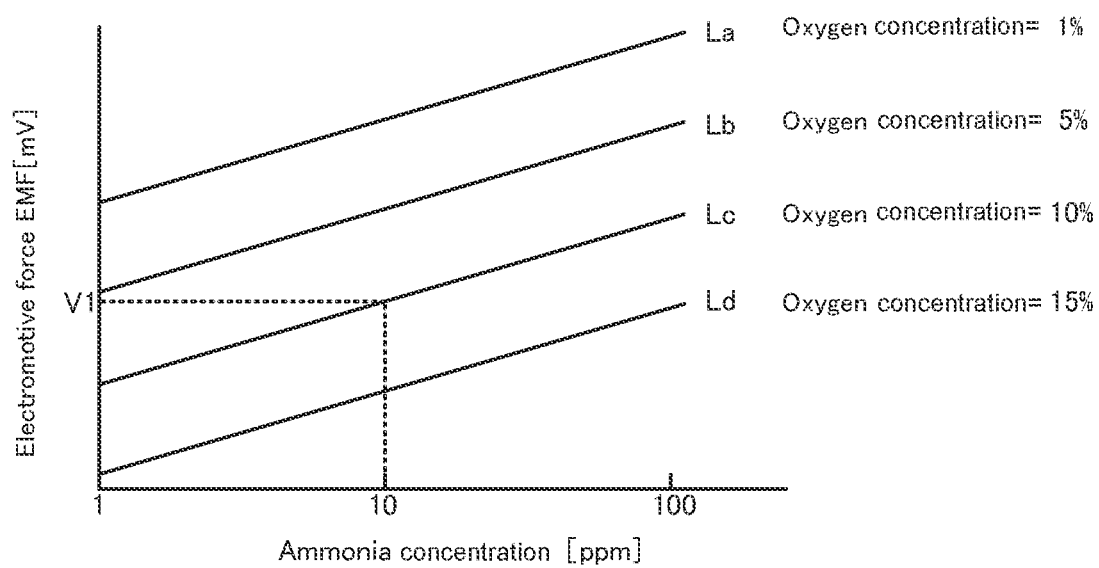
FIG. 4 is a conceptual diagram illustrating measurement correspondence 73 stored in a memory unit 72 included in an ammonia concentration-measuring apparatus 70.

The control unit 71 derives the ammonia concentration in the measurement-object gas on the basis of the electromotive force EMF acquired in Step S210 or the corrected electromotive force derived in Step S215, the oxygen concentration acquired in Step S220, and the measurement correspondence 73 (Step S230). Since the case where the corrected electromotive force has not been derived is described above, the control unit 71 derives the ammonia concentration on the basis of the electromotive force EMF. In this embodiment, the measurement correspondence 73 is the relationship represented by Formula (1) below which has been determined by experiment. FIG. 4 is a conceptual diagram illustrating the measurement correspondence 73 represented by Formula (1).

$$EMF = A \times ln(p_{NH3}) + B \times ln(p_{o2}) + C \qquad (1)$$

(where EMF represents electromotive force [mV]; $p_{NH3}$ represents the ammonia concentration [ppm] in the measurement-object gas; $p_{o2}$ represents the oxygen concentration [%] in the measurement-object gas; and A to C are constants)

In the measurement correspondence 73 according to this embodiment, as illustrated in FIG. 4, the ammonia concentration and the oxygen concentration are associated with the electromotive force EMF such that, the higher the ammonia concentration, the larger the electromotive force EMF, and such that, the lower the oxygen concentration, the larger the electromotive force EMF. Since the horizontal axis in FIG. 4 is a logarithmic axis, the relationship between the logarithm of the ammonia concentration (in Formula (1), $ln(p_{NH3})$) and the electromotive force EMF is represented by a straight line when the oxygen concentration is constant (see the straight lines La to Ld). The measurement correspondence 73 may be a relation as represented by Formula (1) or a map (table containing associated values) as illustrated in FIG. 4. In Step S230, the control unit 71 derives the ammonia concentration on the basis of the measurement correspondence 73. For example, when the electromotive force EMF is the voltage V1 [mV] and the oxygen concentration is 10%, the ammonia concentration derived by the control unit 71 is "10 ppm" (see FIG. 4). After deriving the ammonia concentration in Step S230, the control unit 71 outputs the ammonia concentration to the engine ECU 9 (Step S240) and executes the processing from Step S100.

The measurement correspondence 73 is, for example, a correspondence that has been determined by experiment using the sensor element 31. Normally, the ammonia concentration can be appropriately derived using the measurement correspondence 73 and the electromotive force EMF and the oxygen concentration that have been acquired in Steps S210 and S220, respectively. However, for example, when the gas sensor 30 is used for a prolonged period of time, the above-described change in output characteristics may occur and the correspondence may deviate. The results of the study of the change in output characteristics are described below.

A sensor element 31 including a sensing electrode 51 that was composed of an Au—Pt alloy and had the degree of concentration of 0.92 and an auxiliary electrode 52 composed of Pt was prepared. The sensor element 31 was brought to four different conditions, that is, Conditions 1 to 4, and the output characteristics of the sensor element 31 of each of Conditions 1 to 4 were determined. The sensor element 31 of Condition 1 was prepared as follows. The sensor element 31 was disposed in the exhaust gas passage 3 for the engine 1 (diesel engine) as illustrated in FIG. 1. Subsequently, while the engine 1 was run, the temperature of the mixed potential cell 55 was kept at a predetermined operating temperature (650° C.) with the heater 62 for 2 hours. Then, the engine 1 and the heater 62 were stopped. The sensor element 31 was left in the exhaust gas passage 3 for 24 hours. This sensor element 31 is referred to as "sensor element 31 of Condition 1". The sensor element 31 of Condition 2 was prepared by keeping the temperature of the mixed potential cell 55 at a predetermined operating temperature (650° C.) with the heater 62 for 24 hours in an air atmosphere, subsequently stopping the heater 62, and then leaving the sensor element 31 in the air atmosphere for 24 hours. The sensor element 31 of Condition 3 was prepared as follows. First, the sensor element 31 was disposed in the pipe. Subsequently, while the temperature of the mixed potential cell 55 was kept at a predetermined operating temperature (650° C.) with the heater 62, a model gas (oxygen concentration: 10%, ammonia concentration: 50 ppm, CO concentration: 100 ppm, $C_2H_4$ concentration: 100 ppm, $H_2O$ concentration: 5%, the balance: nitrogen) simulating an exhaust gas was passed through the pipe at a flow rate of 200 L/min. The above condition was maintained for two hours. Subsequently, after the flow of the model gas and the heater 62 had been stopped, the sensor element 31 was left for 24 hours. This sensor element 31 is referred to as "sensor element 31 of Condition 3". The sensor element 31 of Condition 4 was prepared by keeping the temperature of the mixed potential cell 55 at a predetermined operating temperature (650° C.) with the heater 62 for 24 hours in an air atmosphere, subsequently stopping the heater 62, and then heating the sensor element 31 to 850° C.

Figure 5:
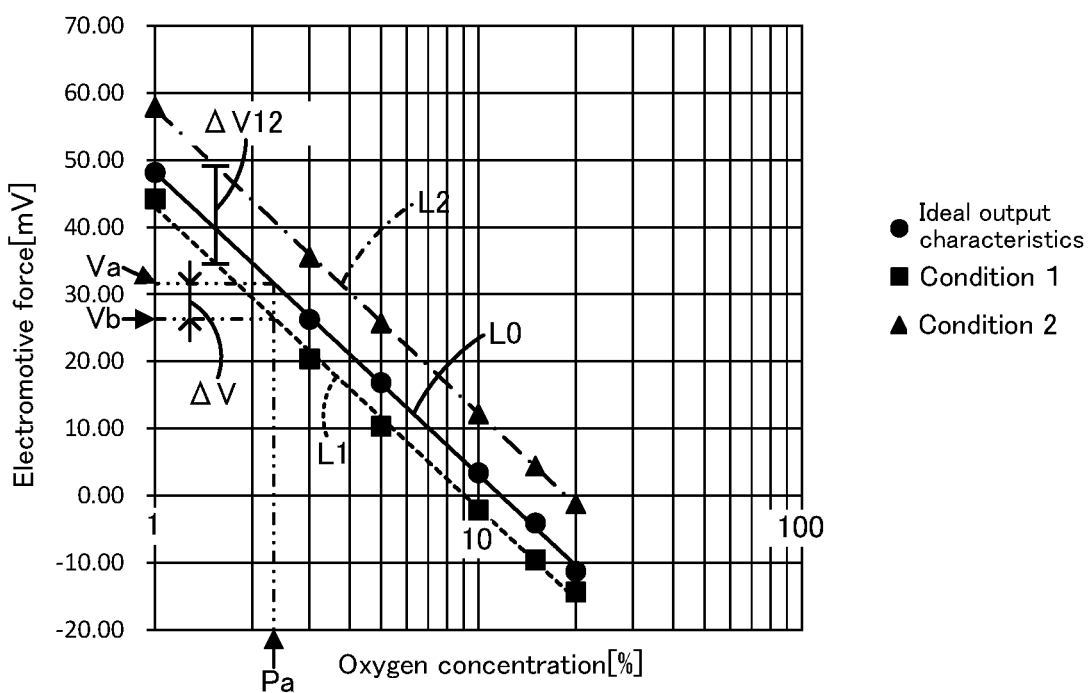
FIG. 5 is a graph illustrating the correspondences between oxygen concentration and electromotive force.

Each of the sensor elements 31 of Conditions 1 to 4 was used for measuring the electromotive force EMF generated under the condition where the sensing electrode 51 was exposed to a model gas that did not include ammonia or a combustible gas. The model gas included 5% $H_2O$ and the balance being oxygen and nitrogen. The electromotive force EMF was measured a plurality of times with different oxygen concentrations. The temperature of the model gas was 120° C. The flow rate of the model gas was 200 L/min. The model gas was passed through a pipe having a diameter of 70 mm, and the sensing electrode 51 of the sensor element 31 was exposed to the model gas inside the pipe. The operating temperature of the mixed potential cell 55 was set to 650° C. Table 1 summarizes the electromotive forces EMF measured using each of the sensor elements 31 of Conditions 1 to 4. Table 1 also shows ideal electromotive forces EMF (ideal output characteristics) that correspond to the respective oxygen concentrations which should be generated under the condition where the sensing electrode 51 is exposed to a gas that does not include ammonia or a combustible gas. Table 1 also shows an expression of ideal output characteristics and the approximation formula (logarithm approximation) of electromotive force of each of Conditions 1 to 4. The expressions of ideal output characteristics and the electromotive forces of the ideal output characteristics shown in Table 1 were derived using the Nernst's equation (Formula (2)) below. FIG. 5 is a graph illustrating the correspondences between oxygen concentration and electromotive force and shows the ideal output characteristics and the output characteristics of each of the sensor elements 31 of Conditions 1 and 2. As is clear from the results shown in Table 1, the electromotive forces of Condition 3 were substantially equal to the electromotive forces of Condition 2, and the electromotive forces of Condition 4 were substantially equal to the electromotive forces of the ideal output characteristics. Therefore, the illustration of Conditions 3 and 4 were omitted because, otherwise, FIG. 5 becomes difficult to view. The straight line L0 in FIG. 5 is the straight line represented by the expression of ideal output characteristics shown in Table 1. The straight lines L1 and L2 in FIG. 5 are the straight lines represented by the approximation formulae of the sensor elements 31 of Conditions 1 and 2 which are shown in Table 1.

$$EMF = (RT/4F) \times ln(P_{o2air}/P_{o2gas}) \qquad (2)$$

(where EMF represents electromotive force [V], R represents gas constant [J/(K·mol)], T represents the temperature [K] of the mixed potential cell 55, F represents Faraday constant [C/mol], $P_{o2gas}$ represents the oxygen concentration [%] in the model gas, and $P_{o2air}$ represents the oxygen concentration [%] in the atmosphere)

TABLE 1

|  |  | Oxygen consentration [%] | | | | | | Approximation on formula<sup>x</sup> |
|---|---|---|---|---|---|---|---|---|
|  |  | 1 | 3 | 5 | 10 | 15 | 20 |  |
| Electromotive force [mV] | Ideal output characteristics | 48.20 | 26.30 | 16.88 | 3.45 | −4.05 | −11.24 | y = −19.55 × ln(x) + 48.173 |
|  | Condition 1 | 44.28 | 20.47 | 10.33 | −2.13 | −9.55 | −14.32 | y = −19.48 × ln(x) + 42.962 |
|  | Condition 2 | 57.90 | 35.62 | 25.80 | 12.20 | 4.42 | −1.20 | y = −19.68 × ln(x) + 57.604 |
|  | Condition 3 | 57.80 | 35.97 | 25.75 | 12.13 | 4.20 | −1.10 | y = −19.71 × ln(x) + 57.654 |
|  | Condition 4 | 48.20 | 26.10 | 16.90 | 3.50 | −4.10 | −12.30 | y = −19.74 × ln(x) + 48.299 |

<sup>x</sup>x is the oxygen concentration [%], y is the electromotive force [mV] in the approximation formula The results of measurement of Conditions 1 to 4 shown in Table 1 and FIG. 5 confirm that the relationship between oxygen concentration and electromotive force varied with the conditions under which the sensor element 31 was used, that is, the change in output characteristics occurred. The change in output characteristics among the sensor elements 31 of Condition 1 to 4 was a change in which only the intercept of the straight line represented by the approximation formula varied by condition while the slope of the straight line remained substantially unchanged. The straight lines represented by the approximation formulae of Conditions 1 to 3 had a slope substantially equal to that of the straight line of the ideal output characteristics, while only the intercepts of the straight lines were deviated from the intercept of the straight line of the ideal output characteristics. The electromotive forces of the sensor element 31 of Condition 4 were substantially equal to the ideal output characteristics. It is considered that the change in output characteristics is caused by impurities (e.g., OH groups dissociated from $H_2O$, CO gas, and sulfur constituents included in a fuel) included in the exhaust gas being deposited on the sensing electrode 51. It is considered that the output characteristics of the sensor element 31 of Condition 4 were the same as the ideal output characteristics because such impurities had been removed by heating at a high temperature (850° C.)

Figure 6:
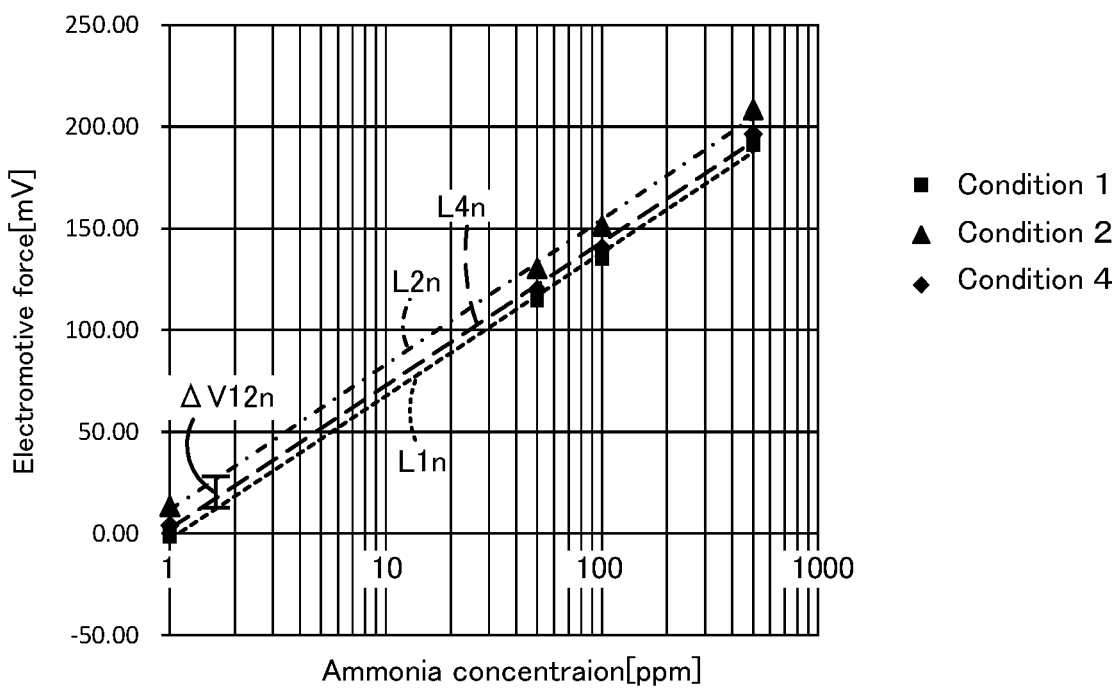
FIG. 6 is a graph illustrating the correspondences between ammonia concentration and electromotive force.
Figure 7:
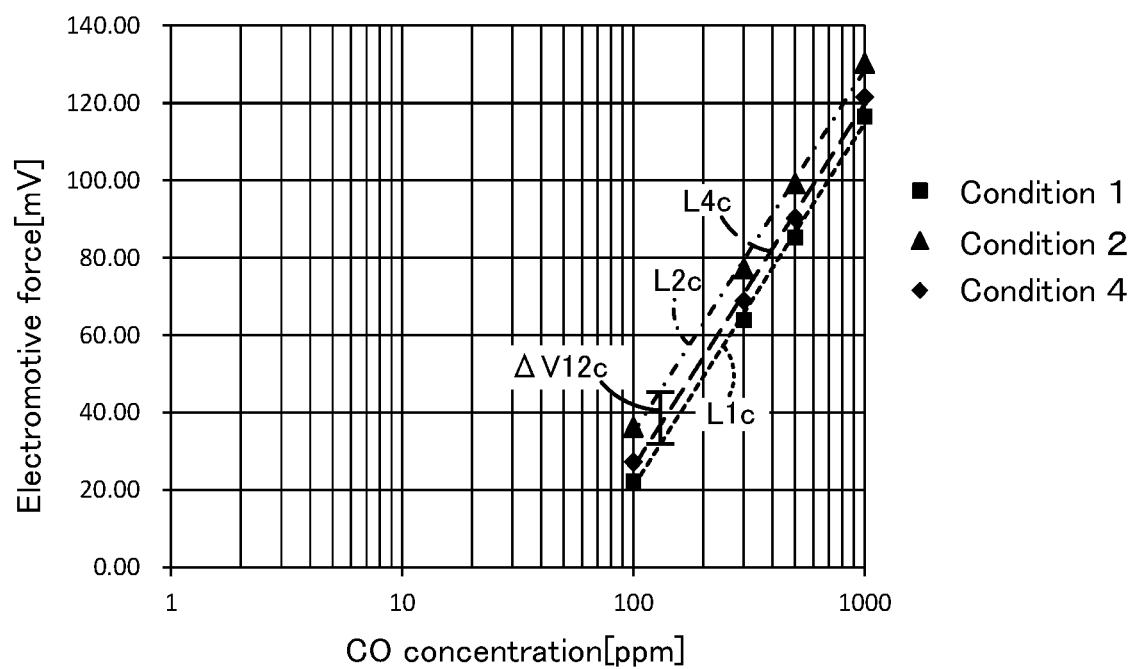
FIG. 7 is a graph illustrating the correspondences between CO concentration and electromotive force.

Each of the sensor elements 31 of Conditions 1 to 4 was used for measuring the electromotive force EMF generated under the condition where the sensing electrode 51 was exposed to a model gas that included at least one of the ammonia and a combustible gas, by the same method as described above. Tables 2 and 3 and FIGS. 6 and 7 show the results. Table 2 and FIG. 6 show the electromotive forces EMF corresponding to the respective ammonia concentrations which were measured when a model gas including ammonia was used. This model gas included 5% $H_2O$, 10% oxygen, and the balance being ammonia and nitrogen. The other measurement conditions were as in the measurement described in Table 1. Table 3 and FIG. 7 show the electromotive forces EMF corresponding to the respective CO concentrations which were measured when a model gas including CO, which is a type of combustible gas, was used. This model gas included 5% $H_2O$, 10% oxygen, and the balance being CO and nitrogen. The other measurement conditions were as in the measurement described in Table 1. Tables 2 and 3 show approximation formulae as in Table 1. In FIGS. 6 and 7, the illustration of Condition 3 is omitted for the sake of simplicity as in FIG. 5. The straight lines L1$n$, L2$n$, and L4$n$ shown in FIG. 6 are the straight lines represented by approximation formulae of the sensor elements 31 of Conditions 1, 2, and 4, respectively, which are shown in Table 2. The straight lines L1$c$, L2$c$, and L4$c$ shown in FIG. 7 are the straight lines represented by approximation formulae of the sensor elements 31 of Conditions 1, 2, and 4, respectively, which are shown in Table 3.

TABLE 2

| | | Ammonia concentraion [ppm] | | | | Approximation formula✕ |
|---|---|---|---|---|---|---|
| | | 1 | 50 | 100 | 500 | |
| Electromotive force [mV] | Condition 1 | −1.34 | 114.64 | 135.16 | 191.00 | y = 30.628 × ln(x) − 2.9367 |
| | Condition 2 | 13.30 | 130.40 | 151.25 | 208.46 | y = 31.046 × ln(x) + 11.513 |
| | Condition 3 | 13.40 | 130.15 | 151.36 | 209.45 | y = 31.151 × ln(x) + 11.365 |
| | Condition 4 | 3.87 | 119.86 | 140.37 | 196.21 | y = 30.627 × ln(x) + 2.2805 |

✕x is the ammonia concentraion[ppm], y is the electromotive force [mV] in the approximation formula

TABLE 3

| | | CO concentraion [ppm] | | | | Approximation formula✕ |
|---|---|---|---|---|---|---|
| | | 100 | 300 | 500 | 1000 | |
| Electromotive force [mV] | Condition 1 | 22.16 | 63.88 | 85.27 | 116.51 | y = 40.798 × ln(x) − 167.03 |
| | Condition 2 | 36.27 | 77.21 | 99.21 | 130.27 | y = 40.689 × ln(x) − 152.61 |
| | Condition 3 | 35.37 | 76.22 | 98.24 | 129.27 | y = 40.647 × ln(x) − 153.33 |
| | Condition 4 | 27.16 | 68.89 | 90.28 | 121.52 | y = 40.798 × ln(x) − 162.03 |

✕x is the CO concentraion[ppm], y is the electromotive force [mV] in the approximation formula The measurement results shown in Table 2 and FIG. 6 confirm that the change in output characteristics among the sensor elements 31 of Conditions 1 to 4 was a change in which only the intercept of the straight line represented by the approximation formula varied by condition while the slope of the straight line remained substantially unchanged. The same applied to the measurement results shown in Table 3 and FIG. 7. Furthermore, the changes in intercept were substantially equal to the changes in the output characteristics measured using a model gas that did not include ammonia or a combustible gas. For example, when the changes in intercept between the sensor elements 31 of Conditions 1 and 2 illustrated in FIGS. 5 to 7 are represented by ΔV12, ΔV12$n$, and ΔV12$c$, respectively, ΔV12, ΔV12$n$, and ΔV12$c$ derived from the approximation fromulae shown in Tables 1 to 3 are ΔV12=14.642 mV (=57.604−42.962), ΔV12$n$=14.4497 mV (=11.513−2.9367), and ΔV12$c$=14.42 mV (=(−152.61)−(−167.06)). That is, ΔV12, ΔV12$n$, and ΔV12$c$ are substantially equal.

It was found from the results shown in Tables 1 to 3 and FIGS. 5 to 7 that the change in output characteristics of the sensor element 31 is a change in which the electromotive force EMF deviates (changes) by substantially the same amount independently of the concentrations of ammonia, a combustible gas, and oxygen. Therefore, if a correction value that compensates for the deviation of the electromotive force EMF caused due to the change in output characteristics can be derived, it becomes possible to derive the concentration of a particular gas with accuracy even after the correspondence has been changed from the stored measurement correspondence 73.

In this embodiment, the measurement correspondence 73 (the relationship represented by Formula (1) and illustrated in FIG. 4) was determined by experiment using the sensor element 31 of Condition 4. Therefore, for example, the straight line Lc illustrated in FIG. 4 and the straight line L4$n$ illustrated in FIG. 6 are straight lines representing the relationship between ammonia concentration and electromotive force EMF at an oxygen concentration of 10% and have substantially the same slope and intercept. The constant A of Formula (1) above is substantially equal to the coefficient (=30.627) of the term of ammonia concentration in the approximation formula of the sensor element 31 of Condition 4 shown in Table 2. Similarly, the constant B of Formula (1) above is substantially equal to the coefficient (=−19.74) of the term of oxygen concentration in the approximation formula of the sensor element 31 of Condition 4 shown in Table 1.

Returning to the description of the control routine illustrated in FIG. 3, when the control unit 71 determines that it is the correction-value derivation time in Step S100, the control unit 71 executes a correction value derivation processing in Steps S110 to S140. In the correction value derivation processing, first, the control unit 71 acquires the electromotive force EMF of the measurement-object gas and the oxygen concentration in the gas (Steps S110 and S120, respectively). The above processing is executed as in Steps S210 and S220 above. Note that, since Steps S110 and S120 are conducted during the correction-value derivation time, that is, while the sensing electrode 51 is exposed to the measurement-object gas which is emitted during fuel cut-off, the electromotive force EMF and the oxygen concentration acquired by the control unit 71 are those of the measurement-object gas which is under the condition where neither ammonia nor a combustible gas is assumed to be included (such a gas is referred to as "correction-value derivation gas"). The electromotive force EMF acquired in this step is referred to as "correction-value derivation electromotive force".

The control unit 71 derives a reference electromotive force that corresponds to oxygen concentration on the basis of the oxygen concentration acquired in Step S120 and reference electromotive force information 74 (Step S130). The reference electromotive force is the electromotive force EMF generated under the condition where the sensing electrode 51 is exposed to a gas that does not include ammonia or a combustible gas before the change in output characteristics occurs. The reference electromotive force information 74 is information concerning the reference electromotive force. In this embodiment, the reference electromotive force information 74 includes the correspondence between oxygen concentration and the reference electromotive force. In this embodiment, the reference electromotive force information 74 is information concerning the correspondence represented by the formula of ideal output characteristics (in FIG. 5, the straight line L0) shown in Table 1. The reference electromotive force information 74 may be a relation or a map (table containing associated values). The reference electromotive force information 74 may be information concerning the correspondence represented by the approximation formula of Condition 4 shown in Table 1. In any case, the reference electromotive force information 74 has been determined using the Nernst's equation or by experiment and stored in the memory unit 72. In Step S130, the control unit 71 derives the reference electromotive force on the basis of the reference electromotive force information 74. For example, in the case where the oxygen concentration in the correction-value derivation gas acquired in Step S120 is Pa [%], the reference electromotive force derived by the control unit 71 is Va [mV] (see FIG. 5).

The control unit 71 derives a correction value that compensates for the difference between the correction-value derivation electromotive force acquired in Step S110 and the reference electromotive force acquired in Step S130 and stores the correction value in the memory unit 72 (Step S140). In this embodiment, the difference between the correction-value derivation electromotive force and the reference electromotive force is directly derived as a correction value. Note that, as described above, the reference electromotive force is an electromotive force EMF generated before the change in output characteristics occurs, while the correction-value derivation electromotive force is an electromotive force reflective of the above-described deviation of electromotive force EMF when the change in output characteristics has occurred. Both correction-value derivation electromotive force and reference electromotive force are electromotive forces generated under the condition where the influences of ammonia and a combustible gas are negligible (or considered negligible). Thus, it is considered that the difference between the correction-value derivation electromotive force and the reference electromotive force corresponds to the deviation of electromotive force which has occurred due to the change in output characteristics. For example, in the case where the sensor element 31 is brought to the same condition as Condition 1 above (the relationship represented by the straight line L1) with use, when the oxygen concentration in the correction-value derivation gas is Pa [%], the correction-value derivation electromotive force is Vb [mV], as illustrated in FIG. 5. The difference between Va and Vb corresponds to the deviation (change in the intercept of the approximation formula described above) in electromotive force which has occurred due to the change in output characteristics. Accordingly, the control unit 71 derives ΔV (=Vb−Va) as a correction in order to compensate for the deviation.

After the control unit 71 has derived and stored the correction value in Step S140, the control unit 71 executes the processing from Step S200. When the control unit 71 executes the concentration derivation processing in Step S215 after the control unit 71 has derived the correction value and stored the correction value in the memory unit 72, the control unit 71 derives a corrected electromotive force by using the correction value. Specifically, the corrected electromotive force derived by the control unit 71 is calculated by subtracting the correction value from the electromotive force EMF acquired in Step S210. In Step S230, the control unit 71 derives the ammonia concentration on the basis of the corrected electromotive force, the oxygen concentration acquired in Step S220, and the measurement correspondence 73. As described above, the change in output characteristics of the sensor element 31 is a change in which the electromotive force EMF deviates (changes) by substantially the same amount independently of the concentrations of ammonia, a combustible gas, and oxygen. Therefore, the actual correspondence between the concentrations of ammonia and oxygen and the electromotive force EMF of the sensor element 31 which holds after the change in output characteristics has occurred is such that the electromotive force EMF deviates from the measurement correspondence 73 illustrated in FIG. 4 by the same amount uniformly. For example, as for the sensor element 31 of Condition 1, the slopes of the straight lines La to Ld illustrated in FIG. 4 do not change and only the intercepts of the straight lines deviate by ΔV illustrated in FIG. 5. In this embodiment, the control unit 71 corrects the electromotive force EMF with the correction value so as to compensate for the deviation. This enables the concentration of a particular gas in the measurement-object gas to be derived using the measurement correspondence 73 with accuracy even after the change in output characteristics has occurred.

Since the control unit 71 derives the correction value each time when the control unit 71 determines that it is the correction-value derivation time in Step S100, the correction value last derived, that is, the latest correction value, may be used in Step S215.

In the ammonia concentration-measuring apparatus 70 according to the embodiment described above in detail, the control unit 71 derives a correction value that compensates for the difference between the correction-value derivation electromotive force acquired at the correction-value derivation time, during which the sensing electrode 51 is exposed to the correction-value derivation gas, and the reference electromotive force derived using the reference electromotive force information 74. In the concentration derivation processing subsequent to the correction-value derivation time, the control unit 71 derives the ammonia concentration in the measurement-object gas by using the correction value. Thus, it is possible to derive, with accuracy, the concentration of a particular gas in the measurement-object gas, even after the change in output characteristics has occurred.

The measurement-object gas is an exhaust gas emitted from an internal-combustion engine. The correction-value derivation gas is an exhaust gas emitted from the internal-combustion engine during fuel cut-off. Since the amounts of ammonia and a combustible gas included in the exhaust gas emitted during fuel cut-off are negligible, using the exhaust gas emitted during the period as a correction-value derivation gas for deriving the correction value enables an appropriate derivation of the correction value. Since the control unit 71 detects the correction-value derivation time on the basis of the fuel cut-off execution information acquired from the engine ECU 9, the control unit 71 is capable of detecting the correction-value derivation time appropriately.

The reference electromotive force information 74 includes the correspondence between the oxygen concentration in a gas that does not include ammonia or a combustible gas and the reference electromotive force generated under the condition where the sensing electrode 51 is exposed to the gas. The control unit 71 derives a reference electromotive force that corresponds to the oxygen concentration in the correction-value derivation gas, which is acquired by the oxygen-concentration acquisition unit 76, on the basis of the reference electromotive force information 74 stored in the memory unit 72. The control unit 71 derives the correction value on the basis of the reference electromotive force and the correction-value derivation electromotive force. Even in the case where the sensing electrode 51 is exposed to a gas that does not include ammonia or a combustible gas, the reference electromotive force and the correction-value derivation electromotive force may vary with the oxygen concentration in the gas as illustrated in FIG. 5. In order to address this, the correspondence between oxygen concentration and the reference electromotive force has been stored and the correction value is derived using a reference electromotive force that corresponds to the oxygen concentration in the correction-value derivation gas. This enables derivation of a further appropriate correction value. Consequently, the accuracy of measurement of particular gas concentration may be further enhanced.

It is needless to say that the present invention is not limited to the above-described embodiment, and that the present invention can be implemented in various embodiments insofar as falling within the technical scope of the present invention.

For example, although the correction-value derivation gas is an exhaust gas emitted from the engine 1 during fuel cut-off in the above-described embodiment, the correction-value derivation gas is not limited to this. The correction-value derivation gas may be any type of measurement-object gas which is under the condition where neither ammonia nor a combustible gas is assumed to be included. For example, the correction-value derivation gas may be the measurement-object gas which is assumed to be the atmosphere. Since the amounts of ammonia and a combustible gas present in the atmosphere are negligible, using such an exhaust gas as a correction-value derivation gas for deriving the correction value enables the control unit 71 to appropriately derive the correction value. In such a case, the control unit 71 may determine whether or not the oxygen concentration acquired by the oxygen-concentration acquisition unit 76 falls within a predetermined range (e.g., 20% to 22%) in which the oxygen concentration acquired by the oxygen-concentration acquisition unit 76 is assumed to be equal to the oxygen concentration in the atmosphere and detect the correction-value derivation time on the basis of the results. This enables the control unit 71 to detect the correction-value derivation time by a relatively easy and simple method. In particular, in the case where the measurement-object gas is an exhaust gas emitted from the engine 1, when the oxygen concentration in the exhaust gas is equal to the oxygen concentration in the atmosphere, it is highly likely that the exhaust gas is an exhaust gas emitted from the engine 1 during fuel cut-off. In other words, it is highly likely that the exhaust gas is under the condition where neither ammonia nor a combustible gas is assumed to be included. Consequently, the control unit 71 can detect the correction-value derivation time appropriately. In the above case, furthermore, the control unit 71 does not necessarily acquire the fuel cut-off execution information from the engine ECU 9.

Although the reference electromotive force information 74 is information that includes the correspondence between oxygen concentration and the reference electromotive force in the above-described embodiment, the reference electromotive force information 74 is not limited to this. For example, the reference electromotive force information 74 may be a reference electromotive force that is an electromotive force EMF generated under the condition where the sensing electrode 51 is exposed to a gas that does not include ammonia or a combustible gas and has an oxygen concentration equal to the oxygen concentration (e.g., 21%) in the atmosphere. In such a case, the control unit 71 may skip Steps S120 and S130 illustrated in FIG. 3 and read the reference electromotive force information 74, that is, the reference electromotive force, from the memory unit 72 instead. For example, in the case where the correction-value derivation gas is the measurement-object gas which is assumed to be the atmosphere (such as an exhaust gas emitted during fuel cut-off), the oxygen concentration in the correction-value derivation gas is substantially equal to the oxygen concentration in the atmosphere. Therefore, the control unit 71 may skip Steps S120 and S130 on the assumption that the oxygen concentration in the correction-value derivation gas be equal to the oxygen concentration in the atmosphere and derive the correction value on the basis of the correction-value derivation electromotive force and the reference electromotive force based on the reference electromotive force information 74. In the above case, the reference electromotive force information 74 is not information represented by the straight line L0 but only one reference electromotive force. This reduces the amount of data of the reference electromotive force information 74. However, it is preferable to use the correspondence between oxygen concentration and reference electromotive force as in the above-described embodiment in order to further enhance the accuracy of the derivation of the concentration of a particular gas.

Although the sensor element 31 includes the concentration cell 56 in order to measure oxygen concentration in the above-described embodiment, the sensor element 31 is not limited to this. That is, the sensor element 31 does not necessarily include the concentration cell 56 (specifically, the auxiliary electrode 52). In such a case, the ammonia concentration-measuring apparatus 70 may acquire oxygen concentration from a device other than the sensor element 31. For example, the ammonia concentration-measuring apparatus 70 may acquire oxygen concentration from another sensor (e.g., an oxygen sensor, an A/F sensor, or a NOx sensor) disposed in the exhaust gas passage 3 or another device (e.g., the engine ECU 9). In such a case, when the oxygen concentration is the oxygen concentration in the measurement-object gas which is measured at a position different from the position of the sensor element 31 in the exhaust gas passage 3, it is preferable to take the time lag (delay time) due to the difference between the position at which oxygen concentration is measured and the position of the sensor element 31 into account. Specifically, the amount of time it takes for the measurement-object gas to flow through the exhaust gas passage 3 from an upstream one of the position of the sensor element 31 and the oxygen concentration measurement position to a downstream one of the two positions is considered as a delay time. The control unit 71 acquires the oxygen concentration in the correction-value derivation gas with the above delay time being taken into account and uses the oxygen concentration for the processing executed in Step S130. Therefore, depending on the amount of delay time, the control unit 71 may store, in the memory unit 72, an oxygen concentration that has been measured at a time prior to the time at which the control unit 71 determines that it is the correction-value derivation time in Step S100 and use the oxygen concentration for the processing executed in Step S130.

Although not particularly described in the above-described embodiment, it is preferable that the change in the output characteristics of the sensor element 31 do not occur (the output characteristics of the sensor element 31 be substantially the same) between the time at which the measurement correspondence 73 is determined and the time at which the reference electromotive force information 74 is predetermined. For example, in the case where the reference electromotive force information 74 used is the ideal output characteristics or the output characteristics of Condition 4, it is preferable to bring the sensor element 31 to the same condition as Condition 4 (e.g., heat at a high temperature) prior to the experiment conducted for determining the measurement correspondence 73. Although the reference electromotive force information 74 used in the above-described embodiment is the ideal output characteristics or the output characteristics of Condition 4, the reference electromotive force information 74 is not limited to this. For example, information concerning the correspondence determined under the condition where the output characteristics have been changed from the ideal output characteristics, such as Condition 1, 2, or 3, may be used as reference electromotive force information 74. In such a case, the measurement correspondence 73 is determined by experiment under the same conditions as described above.

Although the memory unit 72 stores the measurement correspondence 73 and the reference electromotive force information 74 independently in the above-described embodiment, the memory unit 72 is not limited to this. For example, the measurement correspondence 73 may serve also as reference electromotive force information 74. For example, in the case where the measurement correspondence 73 includes the relationship between oxygen concentration and electromotive force EMF at an ammonia concentration of 0 ppm, the control unit 71 may use an electromotive force EMF at an ammonia concentration of 0 ppm which is derived on the basis of the measurement correspondence 73 and the oxygen concentration in the correction-value derivation gas as a reference electromotive force.

Although not particularly described in the above-described embodiment, for example, as is clear from Formula (2), the output characteristics of the mixed potential cell 55 vary also with the temperature T of the mixed potential cell 55, that is, the operating temperature of the sensor element 31 during use. Therefore, it is preferable to determine the measurement correspondence 73 and the reference electromotive force information 74 while the temperature of the mixed potential cell 55 is kept at the same operating temperature by heating. In the case where one sensor element 31 may be used at a plurality of operating temperatures, it is preferable to determine the measurement correspondence 73 and the reference electromotive force information 74 for each of the operating temperatures and store them in the memory unit 72.

Although the particular gas is ammonia in the above-described embodiment, the particular gas is not limited to this. The particular gas may be carbon monoxide (CO) or hydrocarbon (HC). In the case where the particular gas is hydrocarbon, the concentration of the particular gas may be the carbon equivalent concentration of total hydrocarbons. For example, as illustrated in FIG. 7, the correspondence between CO concentration and electromotive force EMF changes such that the electromotive force deviates by the same amount due to the change in output characteristics. Therefore, even in the case where the particular gas is not ammonia, using a correction value that compensates for the difference between the correction-value derivation electromotive force and the reference electromotive force as in the above-described embodiment enables the concentration of the particular gas to be measured with accuracy.

Although the measurement correspondence 73 is the relationship represented by Formula (1) in the above-described embodiment, the measurement correspondence 73 is not limited to this. The measurement correspondence 73 may be any correspondence between the concentrations of a particular gas and oxygen and electromotive force which has been determined by experiment.

Although the engine 1 is a diesel engine in the above-described embodiment, a gasoline engine may be used instead.

What is claimed is:

1. A particular-gas concentration-measuring apparatus that measures a particular gas concentration with a sensor element that includes a mixed potential cell, the mixed potential cell including a solid electrolyte body, a sensing electrode disposed on the solid electrolyte body, and a reference electrode disposed on the solid electrolyte body, the particular gas concentration being a concentration of a particular gas in a measurement-object gas, the particular gas being selected from ammonia and a combustible gas, the particular-gas concentration-measuring apparatus comprising:

an electromotive-force acquisition unit that acquires an electromotive force of the mixed potential cell which is generated where the sensing electrode is exposed to the measurement-object gas;

an oxygen-concentration acquisition unit that acquires an oxygen concentration in the measurement-object gas;

a memory unit that stores a measurement correspondence and reference electromotive force information, the measurement correspondence being a correspondence among the particular gas concentration, the oxygen concentration, and the electromotive force, the reference electromotive force information concerning a reference electromotive force that is the electromotive force generated under a condition where the sensing electrode is exposed to a gas that does not include ammonia or a combustible gas; and a particular-gas concentration derivation unit that executes a concentration derivation processing in which the particular gas concentration corresponding to the electromotive force and the oxygen concentration is derived on the basis of the measurement correspondence, the particular-gas concentration derivation unit causing, at a correction-value derivation time, the electromotive-force acquisition unit to acquire the electromotive force and deriving a correction value compensating for a difference between a correction-value derivation electromotive force that is the electromotive force and the reference electromotive force based on the reference electromotive force information, the correction-value derivation time being time during which the sensing electrode is exposed to a correction-value derivation gas, the correction-value derivation gas being the measurement-object gas that is under the condition where neither ammonia nor a combustible gas is assumed to be included, the particular-gas concentration derivation unit deriving, in the concentration derivation processing executed subsequent to the correction-value derivation time, the particular gas concentration using a corrected electromotive force determined by correcting the electromotive force with the correction value.

2. The particular-gas concentration-measuring apparatus according to claim 1,
wherein the measurement-object gas is an exhaust gas emitted from an internal-combustion engine; and
wherein the correction-value derivation gas is an exhaust gas emitted from the internal-combustion engine during fuel cut-off.

3. The particular-gas concentration-measuring apparatus according to claim 2, further comprising:
an information acquisition unit that acquires fuel cut-off execution information concerning execution of the fuel cut-off,
wherein the particular-gas concentration derivation unit detects the correction-value derivation time on the basis of the fuel cut-off execution information.

4. The particular-gas concentration-measuring apparatus according to claim 1,
wherein the correction-value derivation gas is the measurement-object gas under the condition where neither ammonia nor a combustible gas is assumed to be included and the gas can be assumed to be atmosphere.

5. The particular-gas concentration-measuring apparatus according to claim 4,
wherein the particular-gas concentration derivation unit determines whether or not the oxygen concentration that is acquired falls within a predetermined range in which the oxygen concentration is assumed to be equal to the oxygen concentration in the atmosphere and detects the correction-value derivation time on the basis of a determination that the oxygen concentration is assumed to be equal to the oxygen concentration in the atmosphere.

6. The particular-gas concentration-measuring apparatus according to claim 1,
wherein the reference electromotive force information is information that includes a correspondence between the oxygen concentration in the gas that does not include ammonia or a combustible gas and the reference electromotive force generated where the sensing electrode is exposed to the gas that does not include ammonia or a combustible gas, and
wherein the particular-gas concentration derivation unit derives the reference electromotive force that corresponds to the oxygen concentration in the correction-value derivation gas, the oxygen concentration being acquired by the oxygen-concentration acquisition unit, on the basis of the reference electromotive force information and derives the correction value on the basis of the reference electromotive force and the correction-value derivation electromotive force.

7. A particular-gas concentration-measuring system comprising:
the particular-gas concentration-measuring apparatus and the sensor element according to claim 1.

* * * * *